United States Patent
Kanaya et al.

(10) Patent No.: US 10,239,811 B2
(45) Date of Patent: Mar. 26, 2019

(54) PROCESS FOR PRODUCING REDUCED COENZYME $Q_{10}$

(71) Applicant: KANEKA CORPORATION, Osaka-shi (JP)

(72) Inventors: Kento Kanaya, Takasago (JP); Hiroko Okatsu, Takasago (JP)

(73) Assignee: KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 15/852,719

(22) Filed: Dec. 22, 2017

(65) Prior Publication Data

US 2018/0134644 A1 May 17, 2018

Related U.S. Application Data

(63) Continuation-in-part of application No. PCT/JP2016/068612, filed on Jun. 23, 2016.

(30) Foreign Application Priority Data

Jun. 23, 2015 (JP) .................. 2015-125965

(51) Int. Cl.
| | |
|---|---|
| *C12P 7/66* | (2006.01) |
| *C07C 41/26* | (2006.01) |
| *C07C 46/00* | (2006.01) |
| *C07C 46/08* | (2006.01) |
| *C07C 46/10* | (2006.01) |

(52) U.S. Cl.
CPC .............. *C07C 46/00* (2013.01); *C07C 41/26* (2013.01); *C07C 46/08* (2013.01); *C07C 46/10* (2013.01); *C12P 7/66* (2013.01)

(58) Field of Classification Search
CPC .......... C07C 50/28; C07C 46/06; C07C 46/02
See application file for complete search history.

(56) References Cited

U.S. PATENT DOCUMENTS

| 6,740,338 | B1 | 5/2004 | Chopra | |
|---|---|---|---|---|
| 2005/0069996 | A1 | 3/2005 | Yajima et al. | |
| 2005/0153406 | A1* | 7/2005 | Murata | C12P 7/66 435/133 |
| 2008/0171373 | A1 | 7/2008 | Yajima et al. | |
| 2011/0136191 | A1* | 6/2011 | Yajima | C12P 7/22 435/156 |
| 2012/0059194 | A1 | 3/2012 | Yoshimura et al. | |
| 2013/0142767 | A1 | 6/2013 | Yamacuchi et al. | |
| 2016/0304915 | A1 | 10/2016 | Yajima et al. | |

FOREIGN PATENT DOCUMENTS

| GB | 1591047 | * | 6/1981 |
|---|---|---|---|
| JP | 54-46889 A | | 4/1979 |
| WO | WO 03/056024 A1 | | 7/2003 |
| WO | WO 2010/113900 A1 | | 10/2010 |
| WO | WO 2011/132718 A1 | | 10/2011 |

OTHER PUBLICATIONS

Judy et al, Natural Products Insider, Coenzyme Q10 Facts or Fabrications, 2007, pp. 1-3, recovered from internet at http://www.zmc-usa.com/docs/CoQ10_Facts_or_Fabrications.pdf on Mar. 13, 2018. (Year: 2007).*

* cited by examiner

*Primary Examiner* — Paul A Zucker
(74) *Attorney, Agent, or Firm* — Oblon, McClelland, Maier & Neustadt, L.L.P.

(57) ABSTRACT

A process for producing reduced coenzyme $Q_{10}$ includes removing moisture from an aqueous suspension including a reduced coenzyme $Q_{10}$-containing microbial cell or a disrupted cell thereof such that a de-moisturized substance is obtained and in contact with an oxidizing atmosphere, and that an oxidized coenzyme $Q_{10}$ is produced in an amount of 50 mass % or more relative to a total amount of the oxidized and reduced coenzymes $Q_{10}$, and reducing the oxidized coenzyme $Q_{10}$ outside a microbial cell such that a reduced coenzyme $Q_{10}$ is recovered.

22 Claims, No Drawings

PROCESS FOR PRODUCING REDUCED COENZYME $Q_{10}$

CROSS-REFERENCE TO RELATED APPLICATIONS

The present application is a continuation-in-part of International Application No. PCT/JP2016/068612, filed Jun. 23, 2016, which is based upon and claims the benefits of priority to Japanese Application No. 2015-125965 filed Jun. 23, 2015. The entire contents of these applications are incorporated herein by reference.

TECHNICAL FIELD

The present invention relates to a novel process for producing reduced coenzyme $Q_{10}$.

BACKGROUND ART

In recent years, coenzyme $Q_{10}$ has become widely known to general consumers as supplement or dietary supplement. Coenzyme $Q_{10}$ is a fat-soluble substance having a quinone structure, and "10" in coenzyme $Q_{10}$ is derived from the fact that the number of the repeating units of an isoprene side chain is 10. There are two types of coenzyme $Q_{10}$; oxidized type and reduced type, and oxidized coenzyme $Q_{10}$ has been widely popularized since oxidized coenzyme $Q_{10}$ is inexpensive. However, reduced coenzyme $Q_{10}$ has a higher absorption efficiency, and thus demand for reduced coenzyme $Q_{10}$ has been increasing.

Conventionally, to obtain reduced coenzyme $Q_{10}$, a culture method with reduced coenzyme $Q_{10}$-producing microorganisms is generally used. For example, Patent Literature 1 discloses a method in which microbial cells containing reduced coenzyme $Q_{10}$ at a ratio of not less than 70 mol % are obtained, and produced reduced coenzyme $Q_{10}$ is extracted with an organic solvent. Patent Literature 1 also discloses a method in which the reduced coenzyme $Q_{10}$ is oxidized by an oxidizing agent such as manganese dioxide to produce oxidized coenzyme $Q_{10}$.

CITATION LIST

Patent Literature

[PTL 1] International Publication No. 03/056024

SUMMARY OF THE INVENTION

Problems to be Solved by the Invention

However, in order to efficiently produce reduced coenzyme $Q_{10}$, special means for suppressing production of oxidized coenzyme $Q_{10}$ as a by-product is required. In addition, in the production method for oxidized coenzyme $Q_{10}$ of Patent Literature 1, during oxidization by the oxidizing agent such as manganese dioxide, impurities are produced as by-products due to an oxidization reaction, and it is necessary to remove the impurities. Moreover, it is desirable to avoid use of the oxidizing agent in terms of safety.

Under such a circumstance, an object of the present invention is to provide a novel production method that allows reduced coenzyme $Q_{10}$ to be efficiently, safely, and simply produced.

Solution to the Problems

As a result of thorough research for achieving the above object, the present inventors have found that: when reduced coenzyme $Q_{10}$ is not recovered directly from an aqueous suspension comprising reduced coenzyme $Q_{10}$-containing microbial cells or disrupted cells thereof, but coenzyme $Q_{10}$ is recovered as oxidized coenzyme $Q_{10}$ once and then the oxidized coenzyme $Q_{10}$ is reduced to obtain reduced coenzyme $Q_{10}$, the recovery efficiency of coenzyme $Q_{10}$ itself improves; in oxidizing reduced coenzyme $Q_{10}$, by having a de-moisturized substance (cell) into contact with an oxidizing atmosphere while removing moisture from the aqueous suspension to obtain the de-moisturized substance (cell), coenzyme $Q_{10}$ can be very safely and simply oxidized even without using an oxidizing agent; and, accordingly, reduced coenzyme $Q_{10}$ can be produced at very good efficiency as a whole even though the procedure goes through production of oxidized coenzyme $Q_{10}$ once. Then, the present inventors have made the present invention.

That is, the process for producing reduced coenzyme $Q_{10}$ of the present invention has one or more features described below.

(1) A process for producing reduced coenzyme $Q_{10}$, comprising:

an oxidized coenzyme $Q_{10}$ production step of adjusting a ratio of oxidized coenzyme $Q_{10}$ to 50 mass % or more relative to a total amount of the oxidized and reduced coenzymes $Q_{10}$ by having a de-moisturized cell into contact with an oxidizing atmosphere while removing moisture from an aqueous suspension comprising reduced coenzyme $Q_{10}$-containing microbial cells or disrupted cells thereof to obtain the de-moisturized substance (cell); and a reduced coenzyme $Q_{10}$ recovering step of reducing the oxidized coenzyme $Q_{10}$ produced in the oxidized coenzyme $Q_{10}$ production step, outside microbial cells.

(2) The process for producing reduced coenzyme $Q_{10}$ according to (1), wherein a ratio of the reduced coenzyme $Q_{10}$ contained in the aqueous suspension is not less than 50 mass % relative to the total amount of the oxidized and the reduced coenzymes $Q_{10}$.

(3) The process for producing reduced coenzyme $Q_{10}$ according to (1) or (2), wherein the de-moisturized substance has a final moisture content of not greater than 30 mass %.

(4) The process for producing reduced coenzyme $Q_{10}$ according to any one of (1) to (3), wherein the aqueous suspension comprising microbial cells or disrupted cells thereof has a pH of greater than 4.

(5) The process for producing reduced coenzyme $Q_{10}$ according to any one of (1) to (4), wherein the ratio of the oxidized coenzyme $Q_{10}$ is adjusted to 50 mass % or more relative to the total amount of the oxidized and the reduced coenzymes $Q_{10}$ by drying the aqueous suspension under an oxidizing atmosphere to remove moisture or by drying the aqueous suspension under an oxidizing atmosphere to remove moisture, followed by preservation under an oxidizing atmosphere.

(6) The process for producing reduced coenzyme $Q_{10}$ according to (5), wherein the temperature at the time of removing moisture is not lower than 50° C.

(7) The process for producing reduced coenzyme $Q_{10}$ according to any one of (1) to (6), wherein the ratio of the oxidized coenzyme $Q_{10}$ is adjusted to 80 mass % or more relative to the total amount of the oxidized and the reduced coenzymes $Q_{10}$ in the oxidized coenzyme $Q_{10}$ production step.

(8) The process for producing reduced coenzyme $Q_{10}$ according to any one of (1) to (7), wherein the oxidized coenzyme $Q_{10}$ produced in the oxidized coenzyme $Q_{10}$ production step is extracted and separated from the microbial cells or the disrupted cells thereof, and then the obtained extract is reduced in the reduced coenzyme $Q_{10}$ recovering step.

Advantageous Effects of the Invention

In the present invention, since the reduced coenzyme $Q_{10}$ is brought into contact with the oxidizing atmosphere in a state where moisture has been removed from the aqueous suspension comprising the reduced coenzyme $Q_{10}$-containing microbial cells or the disrupted cells thereof, the reduced coenzyme $Q_{10}$ can be very efficiently and safely oxidized. Since reduced coenzyme $Q_{10}$ is produced by reducing oxidized coenzyme $Q_{10}$ after the oxidized coenzyme $Q_{10}$ is produced once as described above, a decrease in production efficiency due to coexistence of oxidized and reduced coenzymes $Q_{10}$ can be prevented, and reduced coenzyme $Q_{10}$ can be produced efficiently as a whole.

DESCRIPTION OF EMBODIMENTS

The present invention is characterized by comprising:
an oxidized coenzyme $Q_{10}$ production step of adjusting a ratio of oxidized coenzyme $Q_{10}$ to 50 mass % or more relative to a total amount of the oxidized and reduced coenzymes $Q_{10}$ by bringing a de-moisturized substance into contact with an oxidizing atmosphere while removing moisture from an aqueous suspension comprising reduced coenzyme $Q_{10}$-containing microbial cells or disrupted cells thereof to obtain the de-moisturized substance; and
a reduced coenzyme $Q_{10}$ recovering step of reducing the oxidized coenzyme $Q_{10}$ produced in the oxidized coenzyme $Q_{10}$ production step, outside microbial cells.

The reduced coenzyme $Q_{10}$ produced according to the present invention is a compound represented by the following formula (I).

[Chemical formula 1]

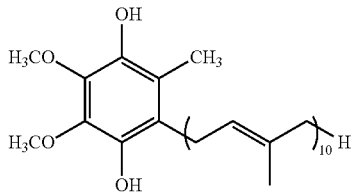

(I)

Further, the oxidized coenzyme $Q_{10}$ is a compound represented by the following formula (II). Hereinafter, the present invention will be described in detail.

[Chemical formula 2]

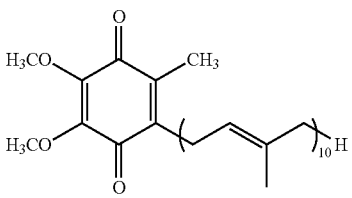

(II)

[Preparation of Aqueous Suspension Comprising Reduced Coenzyme $Q_{10}$-Containing Microbial Cells]

In the present invention, an aqueous suspension comprising reduced coenzyme $Q_{10}$-containing microbial cells or disrupted cells thereof is initially prepared, and oxidized coenzyme $Q_{10}$ is produced from the aqueous suspension. The aqueous suspension comprising the reduced coenzyme $Q_{10}$-containing microbial cells or the disrupted cells thereof can be preferably produced by culturing microorganisms that can produce reduced coenzyme $Q_{10}$ at a ratio of not less than 50 mass % relative to the total amount of oxidized and reduced coenzymes $Q_{10}$ (also referred to as total coenzyme $Q_{10}$ amount). In the present invention, any microorganisms that can preferentially produce reduced coenzyme $Q_{10}$ under actual coenzyme $Q_{10}$-producing conditions can be adopted as reduced coenzyme $Q_{10}$-containing microorganisms. As a simple screening method, for example, microorganisms can also be determined on the basis of whether reduced coenzyme $Q_{10}$ is preferentially produced when products thereof are evaluated by a method in which the microorganisms are cultured with shaking (amplitude: 2 cm, 310 reciprocation/min) at 25° C. for 72 hours in a culture medium (10 mL, (glucose: 20 g, peptone: 5 g, yeast extract: 3 g, malt extract: 3 g)/L, pH: 6.0) using a test tube (inner diameter: 21 mm, overall length: 200 mm).

In the production method of the present invention, microorganisms that produce a reduced coenzyme $Q_{10}$ content of not less than 50 mass % and preferably not less than 60 mass % relative to the total coenzyme $Q_{10}$ amount under actual industrial production culture conditions or under the above culture conditions, are preferably used. Further preferably, microorganisms that have capability to produce reduced coenzyme $Q_{10}$ per culture medium under the actual industrial production culture conditions or under the above culture conditions in an amount of normally not less than 1 μg/mL and preferably not less than 2 μg/mL, are used.

Here, the above reduced coenzyme $Q_{10}$ content and the above ratio of reduced coenzyme $Q_{10}$ in the total coenzyme $Q_{10}$ amount can be confirmed by physically disrupting the microbial cells, then extracting coenzyme $Q_{10}$ with an organic solvent, and performing HPLC analysis. A specific method therefor is not particularly limited. For example, the reduced coenzyme $Q_{10}$ content and the ratio of reduced coenzyme $Q_{10}$ are measured through the following procedure:

1) concentrating a microbial cell-containing broth after culture as necessary, transferring 10 parts by volume of the broth to a test tube with a threaded mouth (inner diameter: 16.5 mm, overall length: 130 mm), and adding 10 parts by volume of glass beads (425 to 600 μm, manufactured by SIGMA-ALDRICH CO. LLC.);

2) adding 3 parts by volume of isopropanol and 18.5 parts by volume of n-hexane relative to 10 parts by volume of the broth under a nitrogen atmosphere;

3) carrying out disruption and extraction of the microbial cells by vigorously shaking for 3 minutes under a nitrogen atmosphere; and 4) evaporating (bath temperature: 40° C.) the obtained hydrophobic organic solvent phase (n-hexane phase) under reduced pressure and analyzing the resultant by HPLC.

Column: YMC-Pack 4.6×250 mm (manufactured by YMC. Co., Ltd.)
Mobile phase: methanol/n-hexane=85/15
Flow rate: 1 mL/min
Detection: UV 275 nm As the reduced coenzyme $Q_{10}$-producing microorganisms usable in the present invention, bacteria, yeasts and fungi may be used without any specific limitation. The specific examples of the above-mentioned microorganisms include microorganisms of the genus *Agrobacterium*, the genus *Aspergillus*, the genus *Acetobacter*, the genus *Aminobacter*, the genus *Agromonas*, the genus *Acidiphilium*, the genus *Bulleromyces*, the genus *Bullera*, the genus *Brevundimonas*, the genus *Cryptococcus*, the genus *Chionosphaera*, the genus *Candida*, the genus *Cerinosterus*, the genus *Exisophiala*, the genus *Exobasidium*, the genus *Fellomyces*, the genus *Filobasidiella*, the genus *Filobasidium*, the genus *Geotrichum*, the genus *Graphiola*, the genus *Gluconobacter*, the genus *Kockovaella*, the genus *Kurtzmanomyces*, the genus *Lalaria*, the genus *Leucosporidium*, the genus *Legionella*, the genus *Methylobacterium*, the genus *Mycoplana*, the genus *Oosporidium*, the genus *Pseudomonas*, the genus *Psedozyma*, the genus *Paracoccus*, the genus *Petromyces*, the genus *Rhodotorula*, the genus *Rhodosporidium*, the genus *Rhizomonas*, the genus *Rhodobium*, the genus *Rhodoplanes*, the genus *Rhodopseudomonas*, the genus *Rhodobacter*, the genus *Sporobolomyces*, the genus *Sporidiobolus*, the genus *Saitoella*, the genus *Schizosaccharomyces*, the genus *Sphingomonas*, the genus *Sporotrichum*, the genus *Sympodiomycopsis*, the genus *Sterigmatosporidium*, the genus *Tapharina*, the genus *Tremella*, the genus *Trichosporon*, the genus *Tilletiaria*, the genus *Tilletia*, the genus *Tolyposporium*, the genus *Tilletiopsis*, the genus *Ustilago*, the genus *Udeniomyces*, the genus *Xanthophllomyces*, the genus *Xanthobacter*, the genus *Paecilomyces*, the genus *Acremonium*, the genus *Hyhomonus*, the genus *Rhizobium* and the like.

In terms of the culture easiness and productivity, bacteria (preferably nonphotosynthetic bacteria) and yeast are preferred. The preferable bacteria include the genus *Agrobacterium*, the genus *Gluconobacter* and the like. The preferable yeast include the genus *Schizosaccharomyces*, the genus *Saitoella* and the like.

The preferable species include *Agrobacterium tumefacience* IFO13263, *Agrobacterium radiobacter* ATCC4718, *Aspergillus clavatus* JCM1718, *Acetobacter xylinum* IFO15237, *Aminobacter aganouensis* JCM7854, *Agromonas oligotrophica* JCM1494, *Acidiphilium multivorum* JCM8867, *Bulleromyces albus* IFO1192, *Bullera armeniaca* IFO10112, *Brevundimonas diminuta* JCM2788, *Cryptococcus laurentii* IFO0609, *Chionosphaera apobasidialis* CBS7430, *Candida curvata* ATCC10567, *Cerinosterus luteoalbus* JCM2923, *Exisophiala alcalophila* JCM12519, *Exobasidium gracile* IFO7788, *Fellomyces fuzhouensis* IFO10374, *Filobasidiella neoformans* CBS132, *Filobasidium capsuloigenum* CBS1906, *Geotrichum capitatum* JCM6258, *Graphiola cylindrica* IFO6426, *Gluconobacter suboxydans* IFO3257, *Kockovaella imperatae* JCM7826, *Kurtzmanomyces nectairei* IFO10118, *Lalaria cerasi* CBS275.28, *Leucosporidium scottii* IFO1212, *Legionella anisa* JCM7573, *Methylobacterium extorguens* JCM2802, *Mycoplana ramosa* JCM7822, *Oosporidium margaritiferum* CBS2531, *Pseudomonas denitrificans* IAM 12023, *Pseudomonas shuylkilliensis* IAM 1092, *Psedozyma aphidis* CBS517.23, *Paracoccus denitrificans* JCM6892, *Petromyces alliaceus* IFO7538, *Rhodotorula glutinis* IFO1125, *Rhodotorula minuta* IFO0387, *Rhodosporidium diobovatum* ATCC1830, *Rhizomonas suberifaciens* IFO15212, *Rhodobium orients* JCM9337, *Rhodoplanes elegans* JCM9224, *Rhodopseudomonas palustris* JCM2524, *Rhodobacter capsulatus* SB1003, *Sporobolomyces holsaticus* IFO1034, *Sporobolomyces pararoseus* IFO0471, *Sporidiobolus johnsonii* IFO1840, *Saitoella complicata* IFO10748, *Schizosaccharomyces pombe* IFO0347, *Sphingomonas parapaucimobilis* IFO15100, *Sporotrichum cellulophilium* ATCC20493, *Sympothomycopsis paphiopedili* JCM8318, *Sterigmatosporidium polymorphum* IFO10121, *Sphingomonas adhesiva* JCM7370, *Tapharina caerulescens* CBS351.35, *Tremella mesenterica* ATCC24438, *Trichosporon cutaneum* IFO1198, *Tilletiaria anomala* CBS436.72, *Tilletia caries* JCM1761, *Tolyposporium bullatum* JCM2006, *Tilletiopsis washintonesis* CBS544, *Ustilago esculenta* IFO9887, *Udeniomyces megalosporus* JCM5269, *Xanthophyllomyces dendrorhous* IFO10129, *Xanthobacter flavus* JCM1204, *Paecilomyces lilacinus* ATCC10114, *Acremonium chrysogenum* ATCC11550, *Hyphomonas hirschiana* ATCC33886, *Rhizobium meliloti* ATCC9930

As the reduced coenzyme $Q_{10}$-producing microorganisms, not only the wild type strains of the above microorganisms but also microorganisms in which the transcription and translation activities of the genes involved in the biosynthesis of reduced coenzyme $Q_{10}$ in the above microorganisms, or the enzyme activities of the expressed proteins are modified or improved can be preferably used, for example.

More preferable microorganisms usable in the present invention are microorganisms that exhibit a reduced coenzyme $Q_{10}$ content of not less than 50 mass %, preferably not less than 60 mass %, more preferably not less than 65 mass %, further preferably not less than 70 mass %, and particularly preferably not less than 80 mass % relative to oxidized and reduced coenzymes $Q_{10}$ when the microorganisms are evaluated by the above culture method and measurement method.

The culture is normally carried out in a culture medium containing macronutrients and micronutrients suited for microorganism proliferation. Examples of the above nutrients include: carbon sources (e.g. carbohydrates such as glucose, sucrose, maltose, starch, corn syrup, and molasses; alcohols such as methanol and ethanol); nitrogen sources (e.g. corn steep liquor, ammonium sulfate, ammonium phosphate, ammonium hydroxide, urea, and peptone); phosphorus sources (e.g. ammonium phosphate and phosphoric acid); and micronutrients (e.g. minerals such as magnesium, potassium, zinc, copper, iron, manganese, molybdenum, sulfuric acid, and hydrochloric acid; vitamins such as biotin, desthiobiotin, and vitamin B1; amino acids such as alanine and histidine; and natural raw materials containing vitamins such as yeast extract and malt extract). However, the above nutrients are not limited thereto, and commonly used nutrients may be used. Natural culture medium components such as yeast extract also contain phosphorus sources such as phosphates. In addition, the above nutrients are used in combination as appropriate.

The pH during the culture can be set as appropriate from the viewpoint of the production efficiency of reduced coenzyme $Q_{10}$, and is, for example, not less than 4, preferably not less than 4.5, and more preferably not less than 5, and is, for example, not greater than 10, preferably not greater than 9, and more preferably not greater than 8.5 (hereinafter, this range is referred to as first pH condition). Furthermore, the pH of the broth influences oxidation efficiency in a later-described oxidization step of reduced coenzyme $Q_{10}$ in which treatment is performed under a low-moisture and oxidizing atmosphere. From the viewpoint of this oxidation efficiency, the pH of the aqueous suspension after the culture is, for example, preferably greater than 4, more preferably not less than 4.5, further preferably not less than 5, and particularly preferably not less than 5.5, and, for example, is preferably not greater than 10, is more preferably not greater than 9, and may be not greater than 8.5, as an upper limit thereof (hereinafter, this range is referred to as second pH condition). In the present invention, one of preferred embodiments is that the pH is adjusted by using an acid and a base, preferably by using a base such that the pH during the culture is adjusted within the first pH condition and the second pH condition is satisfied after the culture, and an oxidization step is executed under a low-moisture and oxidizing atmosphere.

The temperature during the culture is normally 15 to 45° C. and preferably 20 to 37° C. If the temperature during the culture is less than 15° C., the proliferation speed of the microorganisms tends to be too low to be permitted for industrial production. At a higher temperature exceeding 45° C., the viability of the microorganisms tends to be influenced.

In fermentation production on the industrial scale, the concentration of the carbon sources (including produced alcohols) during the culture is preferably controlled to a concentration that causes substantially no adverse effects on the capability to produce coenzyme $Q_{10}$, although it depends on the kind of the microorganisms. Accordingly, it is preferable to control the culture such that the concentration of the carbon sources in the broth becomes a concentration that causes substantially no adverse effects on the capability to produce coenzyme $Q_{10}$, that is, is normally not greater than 20 g/L, preferably not greater than 5 g/L, and more preferably not greater than 2 g/L.

The culture can be terminated at the point of time when the amount of coenzyme $Q_{10}$ produced reaches a desired amount. The culture time is not particularly limited, but is normally 20 to 300 hours, preferably 20 to 200 hours, and more preferably 50 to 100 hours.

The above culture is normally carried out aerobically. Specifically, oxygen is supplied so as not to cause oxygen limitation (oxygen deficiency) during the culture, and the culture is carried out normally under an aeration condition, preferably under an aeration and stirring condition.

By using the above-described microorganisms and culture conditions, microbial cells that contain reduced coenzyme $Q_{10}$ at a ratio of not less than 50 mass % and preferably not less than 60 mass % relative to the total coenzyme $Q_{10}$ amount can be obtained. In addition, the produced amount of reduced coenzyme $Q_{10}$ is, for example, not less than 1 μg/mL, preferably not less than 2 μg/mL, and further preferably not less than 3 μg/mL.

The microbial cells containing reduced coenzyme $Q_{10}$ may be disrupted as necessary. The degree of disruption can be set as appropriate, and, for example, the microbial cells may be disrupted until being torn or fragmented, or may be disrupted so as not to reach such a degree. Even in the case where the microbial cells are not disrupted, coenzyme $Q_{10}$ can be efficiently oxidized in a later-described oxidization step, and thus there is a merit that the process can be simplified without a decrease in oxidation efficiency. However, when the microbial cells are disrupted, there is a merit that the recovery rate improves at the time of later-described extraction of oxidized coenzyme $Q_{10}$ from cells after moisture removal, and thus the disruption of the microbial cells is advantageous in terms of production efficiency.

The above disruption of the microbial cells is carried out by the following one or several disruption methods in optional order. Examples of the disruption methods include, in addition to a physical treatment, a chemical treatment, and an enzymatic treatment, a heating treatment, autolysis, osmotic lysis, and plasmolysis.

Examples of the above physical treatment include use of a high-pressure homogenizer, an ultrasonic homogenizer, a French press, a ball mill, and the like. Examples of the above chemical treatment include a treatment with an acid (preferably a strong acid) such as hydrochloric acid and sulfuric acid, and a treatment with a base (preferably a strong base) such as sodium hydroxide and potassium hydroxide. Examples of the above enzymatic treatment include methods using lysozyme, zymolyase, glucanase, Novozyme, protease, cellulase, and the like. Examples of the above heating treatment include treatments at 60 to 100° C. for approximately 30 minutes to 3 hours. Examples of the above autolysis include treatments with solvents such as ethyl acetate.

The form of the microbial cells to be used for the above cell disruption may be a broth, a concentrated broth, microbial cells collected as wet cells from the broth, a product obtained by washing them, a suspension of the wet cells in a solvent (including, for example, water, physiological saline solution, buffers, and the like), or the like. The preferred is an aqueous suspension of microbial cells, and in terms of operability and the like, the more preferred is the broth, the concentrated broth, or the product obtained by washing them.

The cell concentration in the aqueous suspension of the microbial cells or the disrupted cells thereof is not particularly limited and is normally 1 to 25 wt % on the basis of dry weight. The cell concentration is preferably 10 to 20 wt % in terms of cost.

[Oxidized Coenzyme $Q_{10}$ Production Step]

The aqueous suspension prepared as described above comprises: microbial cells containing reduced coenzyme $Q_{10}$; or disrupted cells thereof. In the present invention, although the final object is reduced coenzyme $Q_{10}$, the obtained reduced coenzyme $Q_{10}$ is not recovered as it is, but is made into oxidized coenzyme $Q_{10}$ in a certain amount or more once. By making reduced coenzyme $Q_{10}$ into oxidized coenzyme $Q_{10}$ once, inefficiency due to coexistence of reduced coenzyme $Q_{10}$ in a large amount can be eliminated. Rather, the reduced coenzyme $Q_{10}$ can be actually produced with the efficiency of the entire process being enhanced.

In the present invention, to oxidize reduced coenzyme $Q_{10}$, moisture is removed from the aqueous suspension, and the obtained de-moisturized substance is brought into contact with an oxidizing atmosphere. According to this method, reduced coenzyme $Q_{10}$ can be simply and safely oxidized even without particularly using an oxidizing agent. Thus, production of impurities that are derived due to use of an oxidizing agent can also be prevented, and an impurity removal treatment becomes unnecessary, so that the production efficiency can be further enhanced.

As timing of contact with the oxidizing atmosphere, when a de-moisturized substance is generated even partially, it is sufficient if the de-moisturized substance and the oxidizing atmosphere are in contact with each other. For example, from an appropriate time such as before or during the moisture removal, the treated matter or the aqueous suspension may be brought into contact with the oxidizing atmosphere. Further, after the moisture removal, the contact with the oxidizing atmosphere may be continued.

The method for contact with the oxidizing atmosphere is not particularly limited, and may be a method in which the treated matter or the aqueous suspension is exposed to the oxidizing atmosphere, or may be a method in which aeration with (sending) the oxidizing atmosphere is performed toward the treated matter or the aqueous suspension.

The final moisture content of the de-moisturized substance obtained after moisture is removed from the aqueous suspension is, for example, preferably not greater than 30 mass %, more preferably not greater than 25 mass %, further preferably not greater than 20 mass %, and particularly preferably not greater than 15 mass %. The lower limit thereof is not particularly limited, and the final moisture content may be not less than 1 mass %, and may be not less than 5 mass %, for example. By decreasing the moisture content, the oxidation efficiency can be enhanced. The oxidizing atmosphere is not particularly limited as long as the oxidizing atmosphere is gas containing oxidizing gas such as oxygen and ozone, but the oxidizing atmosphere is generally preferably the air.

The method for removing moisture from the aqueous suspension is preferably a method in which moisture is removed by vaporization. Specifically, various drying methods may be adopted. In addition, known concentration methods and distillation methods are included in the moisture removing method of the present invention, as long as moisture can be reduced by vaporization so as to fall within a predetermined range. At the time of moisture removal (for example, in removing moisture by means of drying or the like), the treated matter may be heated as appropriate. The temperature at the time of moisture removal (the drying temperature and the like) is not limited. For example, drying under reduced pressure and the like may be performed at room temperature or at a temperature not higher than room temperature, but in the case of heating, the temperature is preferably not lower than 50° C. and more preferably not lower than 70° C. In order to prevent the components of the aqueous suspension from being altered, the temperature at the time of moisture removal (the drying temperature and the like) is preferably not higher than 200° C. and more preferably not higher than 190° C.

The drying method is not particularly limited, and known drying methods such as drying under reduced pressure, drying by heating, or through-flow drying may be adopted as appropriate, and preferable drying methods include spray drying. In the case with the spray drying, the aqueous suspension is sprayed into gas (particularly high-temperature gas, preferably high-temperature air) to be micronized and dispersed, thereby vaporizing moisture rapidly (in several seconds to several tens of seconds). The spray drying has the following merits: since the aqueous suspension is micronized in the spray drying, even when the sprayed microparticles are exposed to high-temperature hot air, a rise in the temperature of the microparticles themselves may be suppressed and thermal history may be reduced, due to vaporization of moisture; and the sprayed microparticles are dried while maintaining spherical shapes thereof, so that the area of contact between the cells after the drying and the oxidizing atmosphere may be increased.

Examples of the spray drying include pressure spraying in which the aqueous suspension is blown out from a nozzle at high pressure, and centrifugal spraying using centrifugal force by a rotary disc. In the case with the spray drying, in order to set the heating temperature within the above-described range, the temperature at the entry of a dryer may be adjusted to preferably 100 to 200° C. and more preferably 150 to 200° C., and the temperature at the exit of the dryer may be adjusted to preferably 50 to 150° C. and more preferably 70 to 120° C. In performing the spray drying, in order to enhance the dispersibility of a liquid or the like, a dispersant may be added to the aqueous suspension as appropriate.

As described above, in the present invention, after the moisture removal, the contact between the treated matter and the oxidizing atmosphere may be further continued. By continuing the contact with the oxidizing atmosphere, an oxidization reaction may be further promoted. Therefore, for example, even when the production rate of oxidized coenzyme $Q_{10}$ is insufficient immediately after drying, the ratio of oxidized coenzyme $Q_{10}$ may be increased by continuing the contact with the oxidizing atmosphere.

In order to continue the contact with the oxidizing atmosphere, it is simple to perform so-called "preservation". The "preservation" refers to an operation in which the de-moisturized substance obtained by drying the aqueous suspension comprising the reduced coenzyme $Q_{10}$-containing microbial cells or the disrupted cells thereof is left under an oxidizing atmosphere for a certain period as it is. The preservation may be performed in a closed container, but is preferably performed in an open container in the case where the amount of the oxidizing atmosphere is insufficient. The preservation period is not particularly limited as long as the ratio of oxidized coenzyme $Q_{10}$ is reached to not less than 50 mass % relative to the total coenzyme $Q_{10}$ amount, but the preservation period is, for example, preferably 1 to 30 days, more preferably 5 to 20 days, and further preferably 10 to 18 days.

The temperature during the preservation is not particularly limited. In order to promote the oxidization reaction, the temperature is preferably not lower than −30° C., more preferably not lower than −10° C., and further preferably not lower than 5° C., and is preferably not higher than 80° C., more preferably not higher than 60° C., and further preferably not higher than 40° C.

The ratio of oxidized coenzyme $Q_{10}$ relative to the total coenzyme $Q_{10}$ amount after the oxidized coenzyme $Q_{10}$ production step is not less than 50 mass %, preferably not less than 60 mass %, further preferably not less than 70 mass %, particularly preferably not less than 80 mass %, and further more preferably not less than 90 mass %. The upper limit thereof is not particularly limited, but the ratio of oxidized coenzyme $Q_{10}$ is preferably 100 mass % and may be not greater than 97 mass %.

[Reduced Coenzyme $Q_{10}$ Recovering Step]

Reduced coenzyme $Q_{10}$ is recovered by reducing the oxidized coenzyme $Q_{10}$ produced in the oxidization step, outside the microbial cells. Reduced coenzyme $Q_{10}$ can be stably and efficiently produced by reducing the oxidized coenzyme $Q_{10}$ after the oxidized coenzyme $Q_{10}$ is produced once.

(1) Extraction Step

After end of the oxidization, the oxidized coenzyme $Q_{10}$ is present together with the microbial cells or disrupted cells thereof. Thus, in the present invention, prior to reducing the oxidized coenzyme $Q_{10}$, preferably, the oxidized coenzyme $Q_{10}$ produced in the oxidized coenzyme $Q_{10}$ production step is extracted and separated from the microbial cells or the disrupted cells thereof, and the obtained extract is reduced in the reduced coenzyme $Q_{10}$ recovering step. In the case where the oxidized coenzyme $Q_{10}$ is reduced and then reduced coenzyme $Q_{10}$ is extracted and separated, the reduced coenzyme $Q_{10}$ may be oxidized during the extraction/separation thereby to decrease the recovery rate. Meanwhile, in the case where extraction/separation is performed in a state as the oxidized coenzyme $Q_{10}$ and reduction is carried out, there is no worry of a decrease in the recovery rate, and reduced coenzyme $Q_{10}$ can be efficiently produced.

In order to extract the oxidized coenzyme $Q_{10}$ from the microbial cells or the disrupted cells thereof, organic solvents such as hydrocarbons, fatty acid esters, ethers, alcohols, fatty acids, ketones, nitrogen compounds (including nitriles and amides), and sulfur compounds can be used.

The hydrocarbons are not particularly limited, but examples of the hydrocarbons include aliphatic hydrocarbons, aromatic hydrocarbons, and halogenated hydrocarbons.

The aliphatic hydrocarbons are not particularly limited, and may be cyclic or acyclic, or saturated or unsaturated. Generally, saturated aliphatic hydrocarbons are preferably used. Normally, aliphatic hydrocarbons having 3 to 20 carbon atoms, preferably 5 to 12 carbon atoms, and more preferably 5 to 8 carbon atoms are used. Specific examples of the aliphatic hydrocarbons include propane, butane, isobutane, pentane, 2-methylbutane, hexane, 2-methylpentane, 2,2-dimethylbutane, 2,3-dimethylbutane, heptane, heptane isomers (e.g., 2-methylhexane, 3-methylhexane, 2,3-dimethylpentane, 2,4-dimethylpentane), octane, 2,2,3-trimethylpentane, isooctane, nonane, 2,2,5-trimethylhexane, decane, dodecane, 2-pentene, 1-hexene, 1-heptene, 1-octene, 1-nonene, 1-decene, cyclopentane, methylcyclopentane, cyclohexane, methylcyclohexane, ethylcyclohexane, p-menthane, and cyclohexene. More preferable are pentane, 2-methylbutane, hexane, 2-methylpentane, 2,2-dimethylbutane, 2,3-dimethylbutane, heptane, heptane isomers (e.g., 2-methylhexane, 3-methylhexane, 2,3-dimethylpentane, 2,4-dimethylpentane), octane, 2,2,3-trimethylpentane, isooctane, cyclopentane, methylcyclopentane, cyclohexane, methylcyclohexane, ethylcyclohexane, and the like.

The aromatic hydrocarbons are not particularly limited. Aromatic hydrocarbons having 6 to 20 carbon atoms are generally used, preferably 6 to 12 carbon atoms, and more preferably 7 to 10 carbon atoms are normally used. Specific examples of the aromatic hydrocarbons include benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, and styrene. Preferred are toluene, xylene, o-xylene, m-xylene, p-xylene, cumene, tetralin, or the like, and cumene is most preferable.

The halogenated hydrocarbons are not particularly limited, and may be cyclic or acyclic, or saturated or unsaturated. Generally, acyclic halogenated hydrocarbons are preferably used. Chlorinated hydrocarbons or fluorinated hydrocarbons are more preferable, and chlorinated hydrocarbons are further preferable. In addition, halogenated hydrocarbons having 1 to 6 carbon atoms, preferably 1 to 4 carbon atoms, and more preferably 1 to 2 carbon atoms are suitably used. Specific examples include dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, and 1,1,1,2-tetrafluoroethane. Preferred are dichloromethane, chloroform, 1,2-dichloroethylene, trichloroethylene, chlorobenzene, 1,1,1,2-tetrafluoroethane, or the like, and chloroform is most preferable.

The fatty acid esters are not particularly limited. Examples of the fatty acid esters include propionates, acetates, formates and the like, and acetates are preferable. Ester functional groups thereof are not particularly limited, but alkyl esters having 1 to 8 carbon atoms or aralkyl esters having 7 to 12 carbon atoms are normally used, and alkyl esters having 1 to 4 carbon atoms are preferably used.

Specific examples of the propionates include methyl propionate, ethyl propionate, butyl propionate, isopentyl propionate, and the like. Ethyl propionate is preferable.

Specific examples of the acetates include methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, and benzyl acetate. Preferred are methyl acetate, ethyl acetate, propyl acetate, isopropyl acetate, butyl acetate, isobutyl acetate, or the like, and most preferred is ethyl acetate.

Specific examples of the formates include methyl formate, ethyl formate, propyl formate, isopropyl formate, butyl formate, isobutyl formate, sec-butyl formate, and pentyl formate. Methyl formate, ethyl formate, propyl formate, butyl formate, isobutyl formate, pentyl formate, and the like are preferable, and ethyl formate is most preferable.

The ethers are not particularly limited, and may be cyclic or acyclic, or saturated or unsaturated. Generally, saturated ethers are preferably used. Normally, ethers having 3 to 20 carbon atoms, preferably 4 to 12 carbon atoms, and more preferably 4 to 8 carbon atoms are used. Specific examples of the ethers include diethyl ether, methyl tert-butyl ether, dipropyl ether, diisopropyl ether, dibutyl ether, dihexyl ether, ethyl vinyl ether, butyl vinyl ether, anisole, phenetole, butyl phenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, and ethylene glycol monobutyl ether. Preferred are diethyl ether, methyl tert-butyl ether, anisole, dioxane, tetrahydrofuran, ethylene glycol monomethyl ether, ethylene glycol monoethyl ether, or the like. More preferred are diethyl ether, methyl tert-butyl ether, anisole, or the like.

The alcohols are not particularly limited, and may be cyclic or acyclic, or saturated or unsaturated. Generally, saturated alcohols are preferably used. Normally, the alcohols have 1 to 20 carbon atoms, preferably 1 to 12 carbon atoms, and more preferably 1 to 6 carbon atoms. Among these alcohols, monohydric alcohols having 1 to 5 carbon atoms, dihydric alcohols having 2 to 5 carbon atoms, or trihydric alcohols having 3 carbon atoms are preferable. Specific examples of the alcohols include: monohydric alcohols such as methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, and 4-methylcyclohexanol; dihydric alcohols such as 1,2-ethanediol, 1,2-propandiol, 1,3-propandiol, 1,2-butanediol, 1,3-butanediol, 1,4-butanediol, 2,3-butanediol, and 1,5-pentanediol; and trihydric alcohols such as glycerol.

As monohydric alcohols, methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, or the like are preferable, and methanol or ethanol are most preferable.

As dihydric alcohols, 1,2-ethanediol, 1,2-propandiol, 1,3-propandiol, and the like are preferable, and 1,2-ethanediol is most preferable. As trihydric alcohols, glycerol is preferable.

Examples of the fatty acids include formic acid, acetic acid, and propionic acid. Formic acid and acetic acid are preferable, and acetic acid is most preferable.

The ketones are not particularly limited, and ketones having 3 to 6 carbon atoms are preferably used. Specific examples of the ketones include acetone, methyl ethyl ketone, methyl butyl ketone, and methyl isobutyl ketone. Acetone and methyl ethyl ketone are preferable.

The nitriles are not particularly limited, and may be cyclic or acyclic, or saturated or unsaturated. Generally, saturated nitriles are preferably used. Normally, nitriles having 2 to 20 carbon atoms, preferably 2 to 12 carbon atoms, and more preferably 2 to 8 carbon atoms are used.

Specific examples include acetonitrile, propionitrile, malononitrile, butyronitrile, isobutyronitrile, succinonitrile, valeronitrile, glutaronitrile, hexanenitrile, heptyl cyanide, octyl cyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methyl cyanobenzoate, methoxybenzonitrile, acetylbenzonitrile, naphthonitrile, biphenylcarbonitrile, phenyl propionitrile, phenylbutyronitrile, methylphenylacetonitrile, diphenylacetonitrile, naphthylacetonitrile, nitrophenylacetonitrile, chlorobenzylcyanide, cyclopropanecarbonitrile, cyclohexanecarbonitrile, cycloheptanecarbonitrile, phenylcyclohexanecarbonitrile, and tolylcyclohexanecarbonitrile. Acetonitrile, propionitrile, butyronitrile, or isobutyronitrile are preferable.

Examples of the nitrogen compounds other than nitriles include amides, such as formamide, N-methylformamide, N,N-dimethylformamide, N,N-dimethylacetamide, and N-methylpyrrolidone, nitromethane, triethylamine, and pyridine.

Examples of the sulfur compounds include dimethyl sulfoxide and sulfolane.

In selecting the organic solvent to be used from among the above organic solvents, properties such as boiling point, viscosity and the like are preferably taken into consideration (e.g., a boiling point that allows appropriate warming for increasing solubility, and that facilitates solvent removal from wet masses by drying and solvent recovery from crystallization filtrates and the like (about 30 to 150° C. under 1 atm); a melting point such that solidification hardly occurs in handling at room temperature or upon cooling to room temperature or lower (not lower than about 0° C., preferably not lower than about 10° C., more preferably not lower than about 20° C.); and a low viscosity (not higher than about 10 cp at 20° C. and the like)).

Examples of preferable organic solvents among the organic solvents include aliphatic hydrocarbons, halogenated hydrocarbons, alcohols, ketones, and nitriles. Among them, preferred are hexane, methanol, ethanol, 1-propanol, 2-propanol, acetone, acetonitrile, or the like. The respective solvents described above may be used solely, or may be mixed and used.

The temperature at the time of extraction is not particularly limited, but is normally 0 to 60° C. and preferably 20 to 50° C.

As the extraction method, it is possible to perform either of batch extraction and continuous extraction (preferably countercurrent multistage extraction). The stirring time in the batch extraction is not particularly limited, but is normally not shorter than 5 minutes. The average retention time in the continuous extraction is not particularly limited, but is normally not shorter than 10 minutes.

The method for separating the extract from the microbial cells or the disrupted cells thereof after the extraction is also not particularly limited, and known solid-liquid separation methods such as filtration and centrifugation may be adopted.

(2) Purification Step

The oxidized coenzyme $Q_{10}$ separated from the cells by the extraction or the like may be reduced as it is, or may be purified and then reduced. It is preferred that the oxidized coenzyme $Q_{10}$ is purified and then reduced, since the purification load after the reduction may be decreased, and oxidized coenzyme $Q_{10}$ is prevented from generating during purification after the reduction thereby to decrease the yield of the reduced coenzyme $Q_{10}$. When the oxidized coenzyme $Q_{10}$ is purified and then reduced, the oxidized coenzyme $Q_{10}$ may be simply and efficiently purified as compared to the case where both reduced coenzyme $Q_{10}$ and oxidized coenzyme $Q_{10}$ are present together, since the ratio of oxidized type in coenzyme $Q_{10}$ at the stage of purification is high.

The purification method is not particularly limited, known purification methods such as column chromatography and crystallization may be adopted, and both may be used in combination. Column chromatography or a combination of column chromatography and another purification method is preferable. Prior to purification, the extract may be concentrated.

(3) Reduction Step

The oxidized coenzyme $Q_{10}$ produced in the oxidized coenzyme $Q_{10}$ production step may be made into reduced coenzyme $Q_{10}$ by being reduced in a reduction step after the above-described pretreatment is performed as necessary. In the reduction step, the oxidized coenzyme $Q_{10}$ is reduced by using a reducing agent. Examples of the reducing agent include ascorbic acids, such as L-ascorbic acid, D-araboascorbic acid, L-ascorbyl palmitate, and L-ascorbyl stearate, sodium borohydride, sodium hydrosulfite, retinal, ß-carotene, tocotrienol, NADH, cyanocobalamin, octyl gallate, dodecyl gallate, sesamol, and thiamine hydrochloride. Sodium hydrosulfite, sodium borohydride, ascorbic acids, and the like are preferable. A natural product, a natural extract, a natural pigment, or the like containing the reducing agent may be used as a reducing agent, and such natural products include royal jelly and KOZU (fragrant vinegar). Such natural extracts include an acerola extract, a pine bark extract, an *Engelhardtia chrysolepis* leaf extract, a *Houttuynia cordata* extract, and enzyme-treated rutin. Such natural pigments include cacao pigment, *gardenia* pigment, grape peel pigment, and monascus pigment.

The reducing agent is preferably added at a ratio of 1 to 50 mol %, more preferably 10 to 30 mol %, and further preferably 15 to 25 mol % relative to the oxidized coenzyme $Q_{10}$.

The temperature in a reduction reaction is preferably 40 to 120° C., more preferably 50 to 110° C., and further preferably 60 to 110° C. from the viewpoint of promoting the reaction. The reaction time is not particularly limited, but is preferably 1 to 50 hours, more preferably 10 to 40 hours, and further preferably 15 to 25 hours.

In the reduction step, the reducing agent and the oxidized coenzyme $Q_{10}$ are often stirred in a reaction solvent. The reaction solvent is not particularly limited unless the reaction solvent has an adverse effect on oxidation/reduction reaction, and may be selected from the same range as the above-described organic solvent for extraction, or may be water or a mixed solvent of an organic solvent and water. In addition, a reaction solvent may not be used, and coenzyme $Q_{10}$ including the oxidized coenzyme $Q_{10}$ may be reacted as oily matter under a heating condition directly with the reducing agent. The organic solvent is not particularly limited, and examples of the organic solvent include alcohols, ketones, nitriles, and ethers, and alcohols such as ethanol are preferable. When an alcohol or the like is used as a solvent in the reduction reaction, the obtained reduced coenzyme $Q_{10}$ may be subsequently purified by crystallization or the like and collected as crystal.

The reduced coenzyme $Q_{10}$ obtained in the reduction step may be further purified by an appropriate method such as concentration, crystallization, and column chromatography. Preferable purification methods are concentration, crystallization, and the like. With these methods, high-purity reduced coenzyme $Q_{10}$ may be collected as solid (particularly, crystal) without oxidizing the reduced coenzyme $Q_{10}$.

According to the present invention, the content of the reduced coenzyme $Q_{10}$ in the solid (preferably, crystal) is very high, and, for example, a content of not less than 98 mass % and more preferably not less than 99 mass % may be achieved.

An aspect of the present invention is a method of efficiently producing oxidized coenzyme $Q_{10}$. The above-described method of producing reduced coenzyme $Q_{10}$ includes a recovering step of reduced coenzyme $Q_{10}$, but when the recovering step is not conducted, the method produces oxidized coenzyme $Q_{10}$ desirably. The present invention thus encompasses a method for producing oxidized coenzyme $Q_{10}$ which includes removing moisture from an aqueous suspension including reduced coenzyme $Q_{10}$-containing a microbial cell or a disrupted cell thereof such that a de-moisturized substance is obtained and in contact with an oxidizing atmosphere, and that an oxidized coenzyme $Q_{10}$ is produced in an amount of 50 mass % or more relative to a total amount of the oxidized and reduced coenzymes $Q_{10}$.

More preferably, the oxidized coenzyme $Q_{10}$ produced is extracted from the microbial cell or its disrupted cell and separated, and the obtained oxidized coenzyme $Q_{10}$ is subjected to column chromatography. As an alternative or in addition to column chromatography, it can be purified by crystallization or the like. More preferably, the oxidized coenzyme $Q_{10}$ produced is extracted from a microbial cell or its disputed cell to separate it, an extract solution containing oxidized coenzyme $Q_{10}$ at a high ratio is obtained, and then after purifying the extract using column chromatography to increase the purity of the oxidized coenzyme $Q_{10}$, further crystallization can be performed to efficiently produce high-purity oxidized coenzyme $Q_{10}$.

Regarding specific procedures for producing the oxidized coenzyme $Q_{10}$ and extraction from microbial cells or disrupted cells thereof, the conditions, methods, and the like described in the method for producing reduced coenzyme $Q_{10}$ can be employed as desired.

In the method for producing the oxidized coenzyme $Q_{10}$, by properly controlling the conditions of the oxidized coenzyme $Q_{10}$ production process, the oxidized coenzyme $Q_{10}$ can be produced at a ratio of 80 mass % or more, preferably 90 mass % or more, relative to the total amount of the oxidized and the reduced coenzymes $Q_{10}$. In such a case, oxidized coenzyme $Q_{10}$ product can be prepared without further purification. If one or more of the purification processes described above are performed, the ratio of the oxidized coenzyme $Q_{10}$ can be further increased.

For example, if the ratio of the oxidized coenzyme $Q_{10}$ produced after the oxidized coenzyme $Q_{10}$ production process is about 80 mass % relative to the total amount of oxidized and reduced coenzyme $Q_{10}$, the ratio can be increased to 90 mass % or more by further carrying out purification. If the ratio of the oxidized coenzyme $Q_{10}$ produced after the oxidized coenzyme $Q_{10}$ production process is about 90 mass % relative to the total amount of oxidized and reduced coenzyme $Q_{10}$, further purification can produce a high-purity oxidized coenzyme $Q_{10}$ substantially free from reduced coenzyme $Q_{10}$.

This is preferable because it does not require an oxidation process that uses an oxidizing agent which was conventionally necessary. When desired, an oxidation process may be carried out using an oxidizing agent to oxidize the remaining reduced coenzyme $Q_{10}$ to further increase the proportion of oxidized coenzyme $Q_{10}$. For example, after extracting the produced oxidized coenzyme $Q_{10}$ from a microbial cell or a disrupted cell thereof and separating it to obtain an extract solution including the oxidized coenzyme $Q_{10}$, a concentrating process or a solvent substitution may be carried out as desired, and an oxidation process as described above can be carried out. Alternatively, such an oxidation process may be carried out after purification of the extract using column chromatography. In the production method according to an embodiment of the present invention, even when such an oxidation step is desired, it is possible to reduce the load of the oxidation process, for example, by using a reduced amount of an oxidizing agent.

EXAMPLES

The present invention will be described in more detail below by means of examples. However, the present invention is not limited by the following examples, and can also be carried out with appropriate modifications being made within the range of the gist described above and below, and any of these modifications are included in the technical scope of the present invention.

[HPLC Analysis Conditions]
Column: YMC-Pack 4.6×250 mm (manufactured by YMC. Co., Ltd.)
Mobile phase: methanol/n-hexane=85/15
Flow rate: 1 mL/min
Detection: UV 275 nm Reference Example 1

*Saitoella complicata* IFO10748 strain, which produces coenzyme $Q_{10}$, was cultured aerobically at 25° C. for 72 hours by using a culture medium (10 L, peptone: 5 g/L, yeast extract: 3 g/L, malt extract: 3 g/L, glucose: 20 g/L, pH: 6.0). The pH of the obtained microbial cell broth was 6.

Example 1

The microbial cell broth obtained in Reference Example 1 was dried under the air atmosphere with a spray dryer (entry temperature: 180° C., exit temperature: 80° C.) to obtain dry cells, and then the dry cells were preserved in an uncapped open glass bottle at room temperature for 12 days. The moisture content of the cells immediately after the drying was 13 wt %. In addition, 10 g of the cells immediately after the drying and 10 g of the dry cells after the preservation were subjected to a batch extraction operation at 60° C. for 60 minutes with ethanol (100 mL), respectively. Thereafter, solid-liquid separation was performed by filtration, and the separated liquid phase was recovered as an extract. When the respective extracts were analyzed by HPLC, the ratios of oxidized coenzyme $Q_{10}$ in coenzyme $Q_{10}$ were 48% and 97%, respectively.

Example 2

The microbial cell broth obtained in Reference Example 1 was dried under the air atmosphere with a spray dryer (entry temperature: 180° C., exit temperature: 80° C.) to obtain dry cells, and then the dry cells were preserved in an uncapped open glass bottle at room temperature for 12 days. The moisture content of the dry cells was 13 wt %. In addition, 0.1 g of the cells immediately after the drying and 0.1 g of the dry cells after the preservation were subjected to a batch extraction operation at room temperature for 30 minutes with a mixed solvent (50 mL) prepared such that the ratio of methanol to chloroform was 3:1, respectively. Thereafter, solid-liquid separation was performed by filtration, and the separated liquid phase was recovered as an extract. When the respective extracts were analyzed by HPLC, the ratios of oxidized coenzyme $Q_{10}$ in coenzyme $Q_{10}$ were 48% and 91%, respectively.

Example 3

A sodium hydroxide aqueous solution (40% (w/w)) was added to the microbial cell broth obtained in Reference Example 1 after the culture, to adjust the pH to 8. This microbial cell broth was dried under the air atmosphere with a spray dryer (entry temperature: 180° C., exit temperature: 80° C.) to obtain dry cells, and then the dry cells were preserved in an uncapped open glass bottle at room temperature for 12 days. The moisture content of the dry cells was 13 wt %. In addition, 0.1 g of the cells immediately after the drying and 0.1 g of the dry cells after the preservation were subjected to a batch extraction operation at room temperature for 30 minutes with a mixed solvent (50 mL) prepared such that the ratio of methanol to chloroform was 3:1, respectively. Thereafter, solid-liquid separation was performed by filtration, and the separated liquid phase was recovered as an extract. When the respective extracts were analyzed by HPLC, the ratios of oxidized coenzyme $Q_{10}$ in coenzyme $Q_{10}$ were 62% and 91%, respectively.

Example 4

The microbial cell broth obtained in Reference Example 1 was dried under the air atmosphere with a spray dryer (entry temperature: 180° C., exit temperature: 80° C.) to obtain dry cells, and then the dry cells were preserved in an uncapped open glass bottle at room temperature for 14 days. The moisture content of the dry cells was 13 wt %. In addition, 15 g of the cells immediately after the drying and 15 g of the dry cells after the preservation were subjected to a batch extraction operation at 50° C. for 60 minutes with hexane (300 mL), respectively. Thereafter, solid-liquid separation was performed by filtration, and the separated liquid phase was recovered as an extract. When the respective extracts were analyzed by HPLC, the ratios of oxidized coenzyme $Q_{10}$ in coenzyme $Q_{10}$ were 48% and 89%, respectively.

Comparative Example 1

The microbial cell broth obtained in Reference Example 1 (1 mL) was subjected to a batch extraction operation at room temperature for 30 minutes with a mixed solvent (50 mL) prepared such that the ratio of methanol to chloroform was 3:1. Thereafter, solid-liquid separation was performed by filtration, and the separated liquid phase was recovered as an extract. When the extract was analyzed by HPLC, the ratio of oxidized coenzyme $Q_{10}$ in coenzyme $Q_{10}$ was 10%.

Comparative Example 2

The microbial cells obtained by the culture in Reference Example 1 were disrupted twice at a disruption pressure of 80 MPa with a pressure homogenizer (manufactured by Rannie) to prepare a microbial cell-disrupted solution containing coenzyme $Q_{10}$. 1 mL of the obtained microbial cell-disrupted solution was subjected to a batch extraction operation at room temperature for 30 minutes with a mixed solvent (50 mL) prepared such that the ratio of methanol to chloroform was 3:1. Thereafter, solid-liquid separation was performed by filtration, and the separated liquid phase was recovered as an extract. When the extract was analyzed by HPLC, the ratio of oxidized coenzyme $Q_{10}$ in coenzyme $Q_{10}$ was 30%.

Comparative Example 3

Concentrated sulfuric acid was added to the microbial cell broth obtained in Reference Example 1 after the culture, to adjust the pH to 4. This microbial cell broth was dried under the air atmosphere with a spray dryer (entry temperature: 180° C., exit temperature: 80° C.) to obtain dry cells, and then the dry cells were preserved in an uncapped open glass bottle at room temperature for 12 days. The moisture content of the dry cells was 13 wt %. In addition, 0.1 g of the cells immediately after the drying and 0.1 g of the dry cells after the preservation were subjected to a batch extraction operation at room temperature for 30 minutes with a mixed solvent (50 mL) prepared such that the ratio of methanol to chloroform was 3:1. Thereafter, solid-liquid separation was performed by filtration, and the separated liquid phase was recovered as an extract. When the respective extracts were analyzed by HPLC, the ratios of oxidized coenzyme $Q_{10}$ in coenzyme $Q_{10}$ were 42% and 49%, respectively.

Comparative Example 4

70 parts by volume of hexane was mixed into 30 parts by volume of a microbial cell-disrupted solution prepared in the same manner as Comparative Example 2, and a batch extraction operation was performed at 45° C. for 60 minutes. Thereafter, when the extract was allowed to stand, rapid oil-water separation was observed, and the volume ratio of the extraction residue relative to the total liquid volume was 0.35. The separated hexane phase was recovered as an extract. When the extract was analyzed by HPLC, the extraction ratio of coenzyme $Q_{10}$ was 60.2%. The prepared extract was concentrated 6 times with an evaporator to obtain an extract-concentrated solution, and the extract-concentrated solution was filtered and then passed through a silica gel normal phase column. However, coenzyme $Q_{10}$ was not satisfactorily fractionated.

TABLE 1

| | Cell broth pH | Drying temperature (° C.) | Preservation period (days) | Preservation conditions | Extraction solvent | Temperature(° C.)/ Time (min) | Immediately after the drying (%) | After preservation (%) |
|---|---|---|---|---|---|---|---|---|
| Example 1 | 6 | 80(out)-180(in) | 12 | Open | Ethanol | 60/60 | 48 | 97 |
| Example 2 | 6 | 80(out)-180(in) | 12 | Open | Methanol 3/ Chloroform 1 | room temperature/ 30 | 48 | 91 |
| Example 3 | 8 | 80(out)-180(in) | 12 | Open | Methanol 3/ Chloroform 1 | room temperature/ 30 | 62 | 91 |
| Example 4 | 6 | 80(out)-180(in) | 14 | Open | Hexane | 50/60 | 48 | 89 |
| Comparative Example 1 | 6 | — | | | Methanol 3/ Chloroform 1 | room temperature/ 30 | 10* | — |
| Comparative Example 2 | 6 | | | Disrupted | Methanol 3/ Chloroform 1 | room temperature/ 30 | 30* | — |
| Comparative Example 3 | 4 | 80(out)-180(in) | 12 | Open | Methanol 3/ Chloroform 1 | room temperature/ 30 | 42 | 49 |
| Comparative Example 4 | 6 | | | Disrupted | Hexane | 45/60 | Insufficient fractionation* | — |

*Although the drying step has not been carried aout, it is described in the same column for comparision.

Example 5

The extract obtained in Example 1 was concentrated 6 times with an evaporator. The obtained extract-concentrated solution was filtered, and then an oxidized coenzyme $Q_{10}$ fraction was fractionated therefrom by using a silica gel normal phase column. The coenzyme $Q_{10}$ fraction solution was dissolved in ethanol, ascorbic acid was added in an amount of 20 mol % relative to coenzyme $Q_{10}$, and a reduction reaction was carried out at 78° C. for 20 hours. The content of reduced coenzyme $Q_{10}$ in reduced coenzyme $Q_{10}$ crystal obtained thereby was 99.6%.

Example 6

Saitoella complicata IFO10748 strain, which produces coenzyme $Q_{10}$, was cultured aerobically at 25° C. for 72 hours by using a culture medium (10 L, peptone: 5 g/L, yeast extract: 3 g/L, malt extract: 3 g/L, glucose: 20 g/L, pH: 6.0).

The pH of the obtained microbial cell broth was 6. This microbial cell broth was dried using a spray dryer (manufactured by GEA NIRO A/S, MOBILE MINOR™ '2000' MODEL E) to obtain dry cells. The moisture content of the dry cells obtained was 15 wt %. Next, the obtained dry cells were put in an uncapped open glass bottle and left to stand in the bottle. After standing for a predetermined period of time, 28 g of the dry cell was sampled, mixed with 200 mL of ethanol, and batch extraction operation was performed at room temperature for 60 minutes. The solid-liquid separation was carried out by filtration, and the separated liquid phase was recovered as an extract and analyzed by HPLC. After preservation of 3 days, 7 days, and 12 days, the ratio of reduced coenzyme $Q_{10}$ was 30%, 12% and 3%, respectively, with respect to the total amount of coenzyme $Q_{10}$.

Example 7

The microbial cell broth obtained by the same culture as in Example 6 was dried using an infrared heating type dryer (manufactured by A & D Co., Ltd., ML-50) to obtain dry cells. The moisture content of the dry cells was 40%. Next, the obtained dry cells were put in an uncapped open glass bottle and left to stand in the bottle. After standing for a predetermined period of time, 1 g of the dry cells was sampled and mixed with 40 mL of hexane, and subjected to a batch extracting operation at room temperature for 1 minute. The solid-liquid separation was carried out by filtration, and the separated liquid phase was recovered as an extract and analyzed by HPLC. The ratio of reduced coenzyme $Q_{10}$ after preservation for 1 day, 6 days and 13 days was 87%, 70% and 42%, respectively, with respect to the total amount of coenzyme $Q_{10}$.

Example 8

The microbial cell broth obtained by the same culture as in Example 6 was dried using a microwave heating dryer (manufactured by AMTek) to obtain a dried microbial cell. 820 g of the dried microbial cells were mixed with 4960 mL of hexane, and a batch extraction operation was performed at room temperature for 60 minutes. After mixing for a predetermined time, solid-liquid separation was carried out by filtration, the separated liquid phase was collected as an extract solution, concentrated 6 times using an evaporator, and the extract concentrate obtained was filtrated, and then using a silica gel normal phase column, the coenzyme $Q_{10}$ fraction was fractionated. Analysis of the obtained coenzyme $Q_{10}$ fraction solution by HPLC revealed that the proportion of oxidized coenzyme $Q_{10}$ in the obtained coenzyme $Q_{10}$ was at least 95%.

Example 9

The extract solution prepared in the same manner as in Example 8 was concentrated 6 times using an evaporator. The obtained extract-concentrated solution was filtered, and then a coenzyme $Q_{10}$ fraction was fractionated therefrom by using a silica gel normal phase column. The coenzyme $Q_{10}$ fraction solution was dissolved in ethanol, ascorbic acid was added in an amount of 20 mol % relative to coenzyme $Q_{10}$, and a reduction reaction was carried out at 78° C. for 20 hours. The content of reduced coenzyme $Q_{10}$ in the obtained coenzyme $Q_{10}$ was 99.8%.

The invention claimed is:

1. A process for producing reduced coenzyme $Q_{10}$, comprising:
   removing moisture from an aqueous suspension comprising a reduced coenzyme $Q_{10}$-containing microbial cell or a disrupted cell thereof such that a de-moisturized substance is obtained and in contact with an oxidizing atmosphere, and that an oxidized coenzyme $Q_{10}$ is produced in an amount of 50 mass % or more relative to the total amount of the oxidized and reduced coenzymes $Q_{10}$; and
   reducing the oxidized coenzyme $Q_{10}$ outside a microbial cell such that a reduced coenzyme $Q_{10}$ is recovered.

2. The process of claim 1, wherein the aqueous suspension, before the removing of the moisture, includes the reduced coenzyme $Q_{10}$ in an amount of not less than 50 mass % relative to the total amount of the oxidized and the reduced coenzymes $Q_{10}$.

3. The process of claim 1, wherein the de-moisturized substance has a moisture content of not greater than 30 mass % after the removing of the moisture.

4. The process of claim 1, wherein the aqueous suspension has a pH of greater than 4 before the removing of the moisture.

5. The process of claim 1, wherein the removing of the moisture comprises drying the aqueous suspension under an oxidizing atmosphere, or
drying the aqueous suspension under an oxidizing atmosphere and preservation for 1 to 30 days under an oxidizing atmosphere.

6. The process of claim 5, wherein the removing of the moisture is conducted at a temperature of not lower than 50° C.

7. The process of claim 1, wherein the removing of the moisture is conducted such that the oxidized coenzyme $Q_{10}$ is produced in an amount of 80 mass % or more relative to the total amount of the oxidized and the reduced coenzymes $Q_{10}$.

8. The process of claim 1, further comprising:
extracting the oxidized coenzyme $Q_{10}$ produced, before the reducing of the oxidized coenzyme $Q_{10}$,
wherein the removing of the moisture comprises drying the aqueous suspension under an oxidizing atmosphere.

9. A process for producing oxidized coenzyme $Q_{10}$, comprising:
removing moisture from an aqueous suspension comprising reduced coenzyme $Q_{10}$-containing a microbial cell or a disrupted cell thereof such that a de-moisturized substance is obtained; and
preserving the de-moisturized substance for 1 to 30 days in an oxidizing atmosphere such that an oxidized coenzyme $Q_{10}$ is produced.

10. The process of claim 9, further comprising:
extracting the oxidized coenzyme $Q_{10}$ produced;
separating an extract including the oxidized coenzyme $Q_{10}$ from the microbial cell or the disrupted cell thereof; and
purifying a separated extract including the oxidized coenzyme $Q_{10}$ by at least one of column chromatography and crystallization.

11. The process of claim 10, further comprising:
oxidizing with an oxidizing agent a residual reduced coenzyme $Q_{10}$ included in the separated extract.

12. The process of claim 9, wherein the de-moisturized substance has a moisture content of not greater than 30 mass % after the removing of the moisture.

13. The process of claim 9, wherein the aqueous suspension has a pH of greater than 4 before the removing of the moisture.

14. The process of claim 9, wherein the removing of the moisture comprises drying the aqueous suspension under an oxidizing atmosphere.

15. The process of claim 1, further comprising, before the reducing of the oxidized coenzyme $Q_{10}$:
extracting the oxidized coenzyme $Q_{10}$ produced;
separating an extract including the oxidized coenzyme $Q_{10}$ from the microbial cell or the disrupted cell thereof; and
purifying a separated extract including the oxidized coenzyme $Q_{10}$ by at least one of column chromatography and crystallization,
wherein the removing of the moisture comprises drying the aqueous suspension under an oxidizing atmosphere.

16. The process of claim 9, wherein the preserving is for 5 to 20 days.

17. The process of claim 9, wherein the preserving is for 10 to 18 days.

18. The process of claim 1, wherein the removing of the moisture comprises drying the aqueous suspension under an oxidizing atmosphere and preservation for 1 to 30 days under an oxidizing atmosphere.

19. The process of claim 1, wherein the reducing of the oxidized coenzyme $Q_{10}$ is conducted such that not less than 98 mass % of reduced coenzyme $Q_{10}$ is obtained with respect to the total amount of the oxidized and reduced coenzymes $Q_{10}$.

20. The process of claim 19, wherein the reducing of the oxidized coenzyme $Q_{10}$ is conducted such that not less than 99 mass % of reduced coenzyme $Q_{10}$ is obtained with respect to the total amount of the oxidized and reduced coenzymes $Q_{10}$.

21. The process of claim 9, wherein the preserving of the de-moisturized substance is conducted such that the oxidized coenzyme $Q_{10}$ is produced in an amount of 50 mass % or more relative to the total amount of the oxidized and reduced coenzymes $Q_{10}$.

22. A process for producing reduced coenzyme $Q_{10}$, comprising:
producing oxidized coenzyme $Q_{10}$ by the process of claim 9;
extracting the oxidized coenzyme $Q_{10}$ produced; and
reducing the oxidized coenzyme $Q_{10}$ outside a microbial cell such that a reduced coenzyme $Q_{10}$ is recovered.

* * * * *